US006866626B2

(12) United States Patent
Long et al.

(10) Patent No.: US 6,866,626 B2
(45) Date of Patent: Mar. 15, 2005

(54) SELF-PROPELLED, INTRALUMINAL DEVICE WITH WORKING CHANNEL AND METHOD OF USE

(75) Inventors: Gary L. Long, Gerards Cross (GB); Kenneth S. Wales, Mason, OH (US)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 101 days.

(21) Appl. No.: 10/247,213

(22) Filed: Sep. 19, 2002

(65) Prior Publication Data

US 2003/0093088 A1 May 15, 2003

Related U.S. Application Data

(60) Provisional application No. 60/344,426, filed on Nov. 9, 2001, and provisional application No. 60/344,429, filed on Nov. 9, 2001.

(51) Int. Cl.[7] ................................................ A61B 1/04
(52) U.S. Cl. ...................................... 600/114; 600/118
(58) Field of Search ................................ 600/114, 115, 600/118, 101, 103, 153, 156, 160

(56) References Cited

U.S. PATENT DOCUMENTS

| | | | |
|---|---|---|---|
| 452,220 | A | 5/1891 | Gunning |
| 4,176,662 | A | 12/1979 | Frazer |
| 4,207,872 | A | 6/1980 | Meiri et al. |
| 4,447,227 | A | 5/1984 | Kotsanis |
| 5,320,091 | A * | 6/1994 | Grossi et al. ............... 600/104 |
| 5,337,732 | A | 8/1994 | Grundfest et al. |
| 5,345,925 | A | 9/1994 | Allred, III et al. |
| 5,398,670 | A | 3/1995 | Stubbe et al. |
| 5,595,565 | A | 1/1997 | Treat et al. |
| 5,599,350 | A | 2/1997 | Schulze et al. |
| 5,604,531 | A | 2/1997 | Iddan et al. |
| 5,709,680 | A | 1/1998 | Yates et al. |
| 6,007,482 | A | 12/1999 | Madni et al. |
| 6,162,171 | A | 12/2000 | Ng et al. |
| 6,224,544 | B1 * | 5/2001 | Takada ........................ 600/155 |
| 6,258,087 | B1 | 7/2001 | Trimmer et al. |
| 6,702,734 | B2 * | 3/2004 | Kim et al. ................... 600/114 |
| 6,709,388 | B1 * | 3/2004 | Mosse et al. ................ 600/114 |

FOREIGN PATENT DOCUMENTS

| | | |
|---|---|---|
| EP | 0 667 115 | 8/1995 |
| EP | 0 827 712 | 11/1998 |
| FR | 2 237 648 | 2/1975 |
| WO | WO 86/06944 | 12/1986 |
| WO | WO 94/05200 | 3/1994 |
| WO | WO 98/11816 | 3/1998 |
| WO | WO 99/30610 | 6/1999 |
| WO | WO 99/32028 | 7/1999 |
| WO | WO 99/34726 | 7/1999 |
| WO | WO 99/53827 | 10/1999 |
| WO | WO 00/22975 A1 | 4/2000 |
| WO | WO 00/44275 | 8/2000 |
| WO | WO 00/76391 A1 | 12/2000 |
| WO | WO 01/08548 | 2/2001 |

OTHER PUBLICATIONS

Christopher P. Swain, MD, The Role of Enteroscopy In Clinical Practice, Endoscopy Journal vol. 9, No. 1, Jan. 1999, pp. 135–143 Jan. 1999.

Blair S. Lewis, MD The History of Enteroscopy Journal vol. 9, No. 1, Jan. 1999, pp. 145–161.

C. Mosse et al. Electrical stimulation for propelling endoscopes, Gastrointestinal Endoscopy 54, No. 1, 2001, pp. 79–83.

(List continued on next page.)

*Primary Examiner*—Beverly M. Flanagan

(57) ABSTRACT

The present invention provides apparatus and method for providing access of a medical instrument, such as a surgical instrument, from a point outside the patient's body to a point within a body lumen, such as a portion of the Gastrointestinal tract. A self propelled device, such as a capsule having electrodes for providing contraction of lumen tissue, can be positioned within the body lumen at a desired location. The medical instrument can be directed through a working channel associated with the capsule to access the body lumen tissue through the capsule.

24 Claims, 10 Drawing Sheets

OTHER PUBLICATIONS

Charles Alexander Mosse, BA MSC and C. Paul Swain, MD, Technical Advances and Experimental Devices for Enteroscopy Journal vol. 9, No. 1, Jan. 1999, pp. 145–161.

Given® Imaging Capsule, Given® Diagnostic Imaging System Now Available in the USA, p. 1 "WebPage Print Data" Date: Aug. 2, 2001.

Given Imaging Ask the Expert pp. 1–2 "Web Page Print Data" Date: Aug. 2, 2001.

Given* Imaging Expanding the Scope of GI "Web Page Print Data" p. 1: Date Aug. 2, 2001.

Given* Imaging M2A™ About M2A ™ Viewing the Small Intestine p. 1 "Web Page Print Data" Date: Aug. 2, 2001.

Given* "Imaging About M2A Given® Diagnostic Imaging System p. 1 Web Page Print Data" Date: Aug. 2, 2001.

Given* Imaging About M2A™ The Procedure, p. 1 "Web Page Print Data" Date: Aug. 2, 2001.

Given* Imaging About M2A™ Viewing the Results, p. 1 "Web Page Print Data" Date: Aug. 2, 2001.

OE Reports Technology and Trends for the International Optical Engineering Community, pp. 1–3 No. 200, Aug. 2000.

New England Journal of Medicine, vol. 344, No. 3, Jan. 18, 2001, PP232–233.

International Search Report dated Apr. 24, 2003 for corresponding EPO application.

* cited by examiner

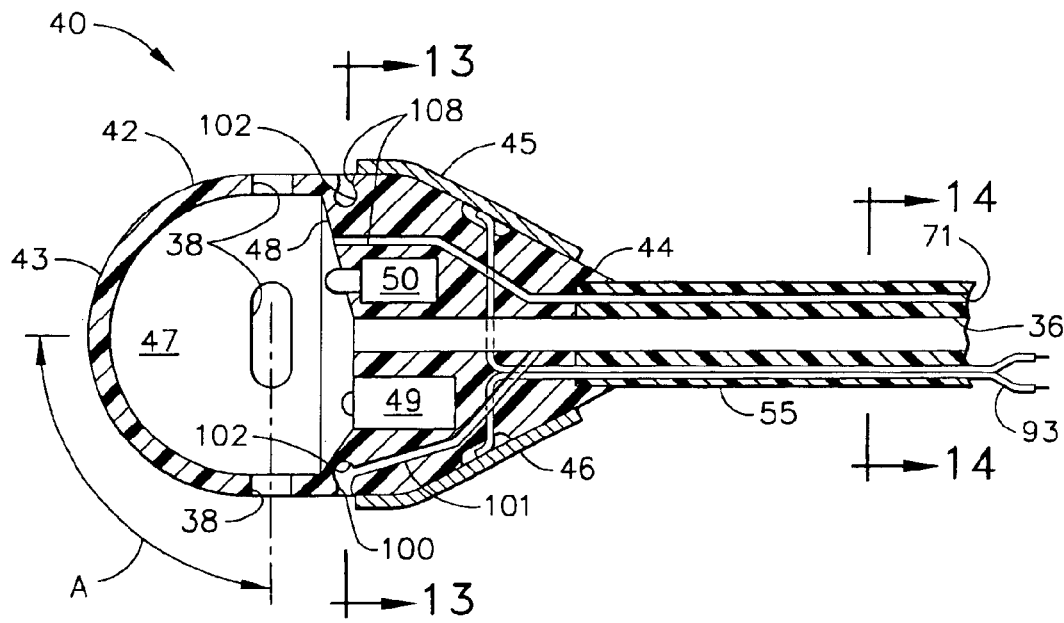
FIG. 12
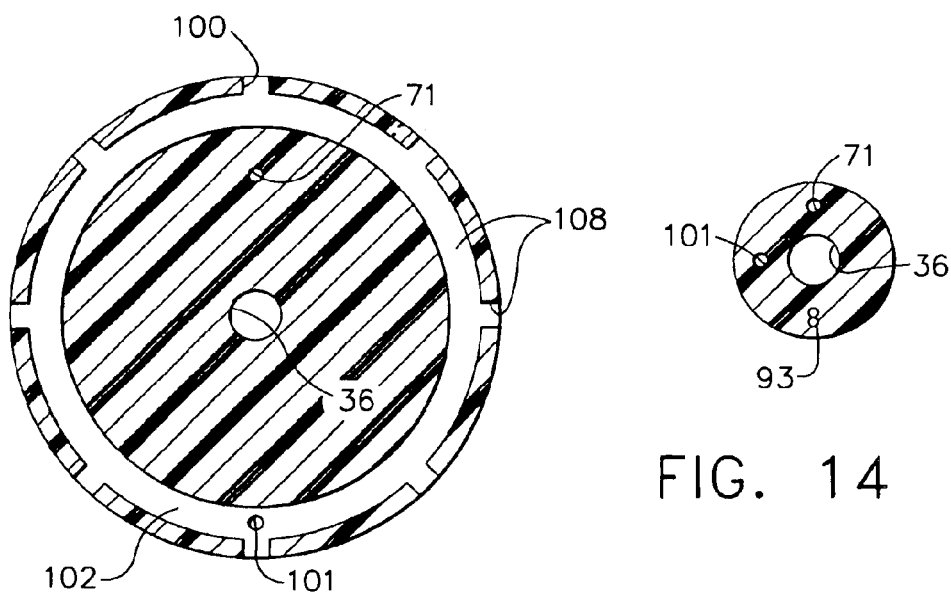
FIG. 13
FIG. 14

SELF-PROPELLED, INTRALUMINAL DEVICE WITH WORKING CHANNEL AND METHOD OF USE

This application claims priority to the following provisional patent applications: "Method for Providing Access to Luminal Tissue", Ser. No. 60/344,426, filed Nov. 9, 2001 in the name of Long et al.; and "Luminal Propulsive Device Having a Generally Continuous Passageway", Ser. No. 60/344,429, filed Nov. 9, 2001 in the name of Long et al.

FIELD OF THE INVENTION

The present invention relates to a medical device that self-propels within a lumen of a patient's body.

BACKGROUND

A physician typically accesses and visualizes tissue within a patient's gastrointestinal (GI) tract with a long, flexible endoscope. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel, typically about 2.5–3.5 mm in diameter, extending from a port in the handpiece to the distal tip of the flexible shaft. A physician may insert medical instruments into the working channel to help diagnose or treat tissues within the patient. Physicians commonly take tissue biopsies from the mucosal lining of the GI tract using a flexible, biopsy forceps through the working channel of the endoscope.

Insertion of a flexible endoscope, especially into the colon, is usually a very time-consuming and uncomfortable procedure for the patient, even when sedated with drugs. A physician often needs several minutes to push a flexible endoscope through the convoluted sigmoid, descending, transverse, and ascending portions of the colon. The physician may diagnose and/or treat tissues within the colon either during insertion or removal of the endoscope. Often the flexible endoscope "loops" within the colon, such as at the sigmoid colon or at the splenic flexure of the colon, so that the endoscope can stretch the portion of colon containing it. This stretching can cause pain to the patient even though sedation is used. Depending on the anatomy of the patient and the skill of the physician in manipulating the flexible endoscope, some portions of the colon may be unexamined, thus increasing the risk of undiagnosed disease.

Given® Engineering LTD, Yoqneam, Israel, sells a device in the U.S. called the M2A™ Swallowable Imaging Capsule. The device contains a tiny video camera, battery, and transmitter. It is propelled through the gastrointestinal tract by natural peristalsis. The device is currently used for diagnostic purposes and passes through the intestinal tract with a velocity determined by the natural, peristaltic action of the patient's body. World Publication WO 0108548A1 filed by C. Mosse, et al. describes a self-propelling device adapted to travel through a passage having walls containing contractile tissue. The applicants disclose that the device is particularly useful as an enteroscope and may also carry objects such as feeding tubes, guide wires, physiological sensors or conventional endoscopes within the gut. A summary of other alternatives to push endoscopy can be found in "*Technical Advances and Experimental Devices for Enteroscopy*" by C. Mosse, et al, published in Gastrointestinal Endoscopy Clinics of North America, Volume 9, Number 1, January 1999: pp. 145–161.

During each procedure, a physician typically needs to pass medical instruments in and out of the colon numerous times. Current endoscopes have working channels (also called biopsy channels) for passing instruments into the lumen for performing procedures on the lumen wall with endoscopic visualization. It is important that variations of a self-propelled intraluminal device also have such an integral working channel for the passage of instruments into the lumen, rather than requiring that a separate endoscope with a working channel be pulled behind the self-propelled device. Reducing what must be carried into the lumen may minimize the contractile force of the luminal walls required for self-propulsion of the device. In addition, the need for a conventional endoscope may be completely eliminated, along with associated costs, if a self-propelled device also had an integral working channel for performing diagnosis and/or therapy inside the lumen.

Currently physicians also use stains such as methylene blue dye, or contrast agents such as indigo carmine, to identify diseased tissues within the lumen of the colon or esophagus. Such stains and agents, which we shall generally refer to hereinafter as diagnostic agents, may be passed into the lumen via the working channel of the endoscope. The diagnostic agent highlights the diseased tissue, such as a polyp or a cancerous lesion, for identification by the physician. Applying diagnostic agents may be messy and require special additional steps during and after the examination procedure, including the thorough removal of the diagnostic agent from the endoscope prior to reuse on another patient. The ability to apply a minimal amount of such diagnostic agents evenly on the luminal wall, rather than washing the luminal wall with large amounts of diagnostic agent that then collects in the lumen or drains onto the examination table, for example, is an attractive option for physicians. Also, using a low cost, potentially disposable device such as a self-propelled intraluminal device provides physicians with a desirable alternative to cleaning the diagnostic agent from a conventional, reusable, flexible endoscope.

What is needed, therefore, is a self-propelled, intraluminal device that includes an integral, working channel for the passage of medical instruments in order to treat tissues in the lumen. What is also needed is a self-propelled, intraluminal device that dispenses a diagnostic agent to identify diseased tissue in the lumen.

SUMMARY OF THE INVENTION

In one embodiment, the present invention provides a medical device which can be used for medical diagnosis and/or treatment of a body lumen, such as the GI tract. The medical device comprises a self propelled movable device capable of travel through a patient's body lumen, and a working channel associated with the movable device for providing access to at least a portion of the lumen through the movable device from a point outside the patients body. A vacuum source can be operatively associated with the movable device for communicating vacuum to the body lumen.

The medical device can be self propelled by stimulation of tissue within the lumen, such as with an electrode for providing electrical stimulation and contraction of muscle tissue.

A portion of the working channel can be disposed in an umbilicus, and a portion of the working channel can be disposed in the movable device, which can be a capsule. The capsule can include one or more openings in its exterior surface, the openings being in communication with, or forming part of, the working channel.

The present invention also provides a method of accessing tissue in a body lumen. The method comprises the steps of providing a self propelled device, positioning the self propelled device in the body lumen, and directing a medical instrument from a point outside the body to access tissue in the lumen through the self propelled device. The method can include the step of drawing tissue into a portion of the self propelled device. In one embodiment, the method comprises the step of surgically removing a portion of the patient's body through the self propelled device, then through the umbilicus to a point external of the patient.

BRIEF DESCRIPTION OF THE DRAWINGS

We have set forth the novel features of the invention with particularity in the appended claims. To fully understand the invention, however, please refer to the following description and accompanying drawings.

FIG. 12 is a sectional view of capsule 40 of FIG. 11.

FIG. 13 is a cross sectional view of capsule 40 taken at lines 13—13 in FIG. 12.

FIG. 14 is a cross sectional view of umbilicus 55 of capsule 40 shown in FIG. 12 and taken at line 14—14.

DETAILED DESCRIPTION OF THE INVENTION

The present invention is a self-propelled intraluminal medical device including one or more of the improvements previously listed. By way of example, the present invention is illustrated and described for application in the colon of a human patient. However, the present invention is applicable for use in other body lumens in humans and in other mammals.

Figure 1:
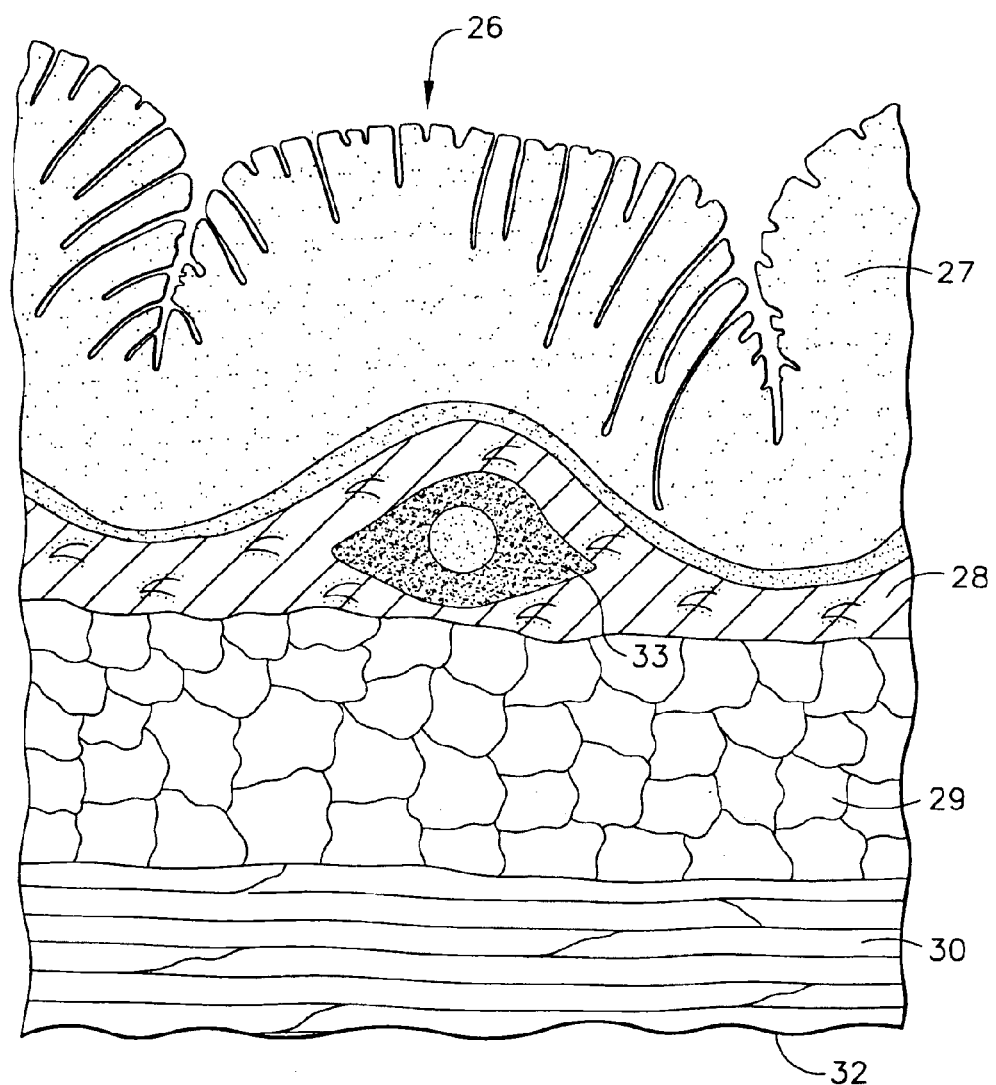
FIG. 1 is a cross sectional view of a portion of the gastrointestinal tract such as the colon.

FIG. 1 shows a section of a wall 26 of the mammalian colon, and includes a mucosal layer 27, a submucosal layer 28 (shown with a lymph node 33), a circular muscular layer 29, a longitudinal muscular layer 30, and a serosa 32. Natural peristalsis is a progressive wavelike contraction of wall 26 that occurs involuntarily and is normally stimulated by distention of the wall 26 from the contents within. Circular muscular layer 29 and longitudinal muscular layer 30 comprise the contractile tissue and contract when electrically stimulated, causing an instantaneous circumferential reduction of that portion of the lumen.

Figure 2:
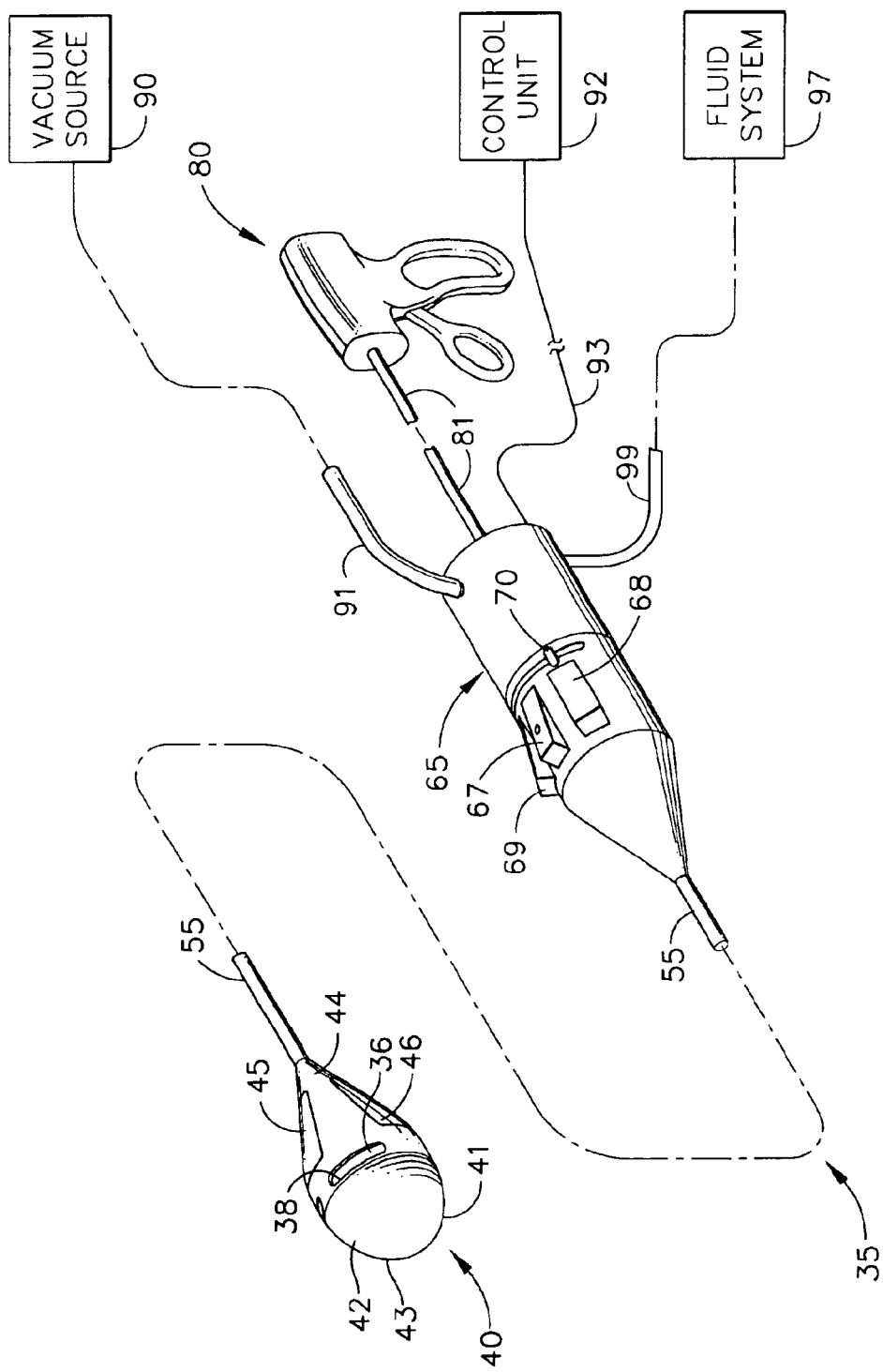
FIG. 2 shows a first embodiment of the present invention, a medical device 35 that includes a capsule 40, an umbilicus 55, a handpiece 65, a control unit 92, a vacuum source 90, and a fluid system 97.

FIG. 2 shows a medical device 35 of the present invention which, in one embodiment, comprises a capsule 40, an umbilicus 55, a handpiece 65, a vacuum source 90, a control unit 92, and a fluid system 97. Capsule 40 is generally egg-shaped in this embodiment and sized to slide easily through the anus of the patient. Capsule 40 comprises a body 41 with an exterior surface 42, a leading end 43, a trailing end 44. Leading end 43 can be rounded to provide an atraumatic or blunt leading surface for navigating the torturous twists of the colon. Trailing end 44 of capsule 40 can be tapered, such as with a generally conical shape, to provide forward thrust when squeezed by the constriction of colon. Other suitable shapes for capsule 40 are possible. In general, capsule 40 can have a smooth exterior surface 42 which is streamlined for sliding passage through the body lumen. Body 41 can include one or a plurality of windows 38 providing openings through the exterior surface 42 to provide access from a working channel 36 (FIG. 3) that extends through umbilicus 55 and handpiece 65 to positions exterior of the capsule 40. A first electrode 45 having a first electrical polarity and a second electrode 46 having a second electrical polarity can be disposed on the capsule 40, such as by being mounted on exterior surface 42 of trailing end 44. Umbilicus 55 connects trailing end 44 to handpiece 65 and can be approximately as long as the flexible shaft of a colonoscope. For instance, the umbilicus 55 can extend at least 1 meter, and in one embodiment can have a length of about about 1.7 meters.

Capsule 40 can be constructed from one or more of numerous materials that are rigid relative to the soft tissue of the body. These materials include metals, elastomers, and plastics. Preferably, capsule 40 is made from injection molded plastic in two or more pieces that are assembled with the other components. Suitable plastics include, but are not limited to, polycarbonate, polyetherimide, and polyethylene.

Handpiece 65 in FIG. 2 can include a vacuum control 67, a motion control 68, a frequency control 69, and a current control 70. A medical instrument 80 which can be used in conjunction with medical device 35 may include a flexible shaft 81, which is shown inserted into the proximal end of working channel 36 of medical device 35. Medical instrument 80 is representative of numerous therapeutic or diagnostic devices commercially available, including a conventional, endoscopic biopsy forceps such as the Microvasive brand, "Radial Jaw 3" Single-Use Biopsy Forceps, Catalog No. 1599, from Boston Scientific, Natick, Mass. Medical instrument 80 may be inserted and withdrawn from working channel 36 repeatedly during a medical procedure while capsule 40 and a portion of umbilicus 55 are inserted in the colon. The operator may evacuate fluids and air from the colon using vacuum control 67, which fluidly connects a hose 91 from vacuum source 90 to capsule 40. By applying vacuum, the operator may also cause a portion of the colon to collapse and come into more intimate contact with first electrode 45 and second electrode 46, thus improving electrical connectivity to the contractile tissue in the colon. Motion control 68, frequency control 69 and current control 70 allows the operator to adjust electrical input to first electrode 45 and second electrode 46 during the medical procedure.

In FIG. 2, control unit 92 is shown operatively connected to handpiece 65 by wiring 93 to provide electrical pulses of a desired frequency to first electrode 45 and second electrode 46 of capsule 40. Control unit 92 can comprise a frequency generator that provides at least one electrical waveform. Suitable waveforms include sinusoidal waves, square waves, triangular waves, and combinations. Control unit 92 also includes a constant current source, such as the Stimulus Isolator commercially available from World Precision Instruments of Sarasota, Fla.

Motion control switch 68 activates and deactivates the intraluminal propulsion of capsule 40. Frequency control 69 varies electrical stimulation pulse frequency, which may be generally uniform or varying. Current control 70 varies electrical stimulation current amperage.

In one embodiment, the electrical stimulation frequency may be approximately in the range of 5 to 20 Hz, although frequency may be as high as 1000 Hz. Electrical stimulation current amplitude may be approximately in the range of 10 to 50 mA, and as high as 100 mA. These parameters may be adjustable by the operator or set to predetermined values in control unit 92. One particularly suitable electrical stimulation type is a half duty cycle, 15 Hz, 30 mA square wave.

Figure 3:
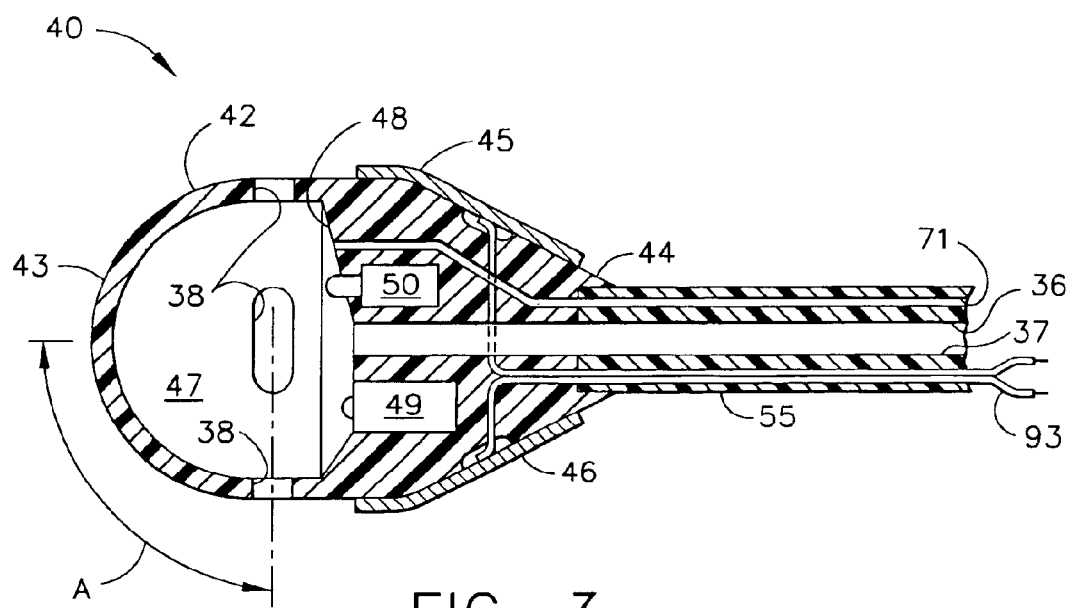
FIG. 3 is a sectional view of capsule 40 of medical device 35 shown in FIG. 2, and includes a first electrode 45 and a second electrode 46, and showing the distal portion of a working channel 36.
Figure 9:
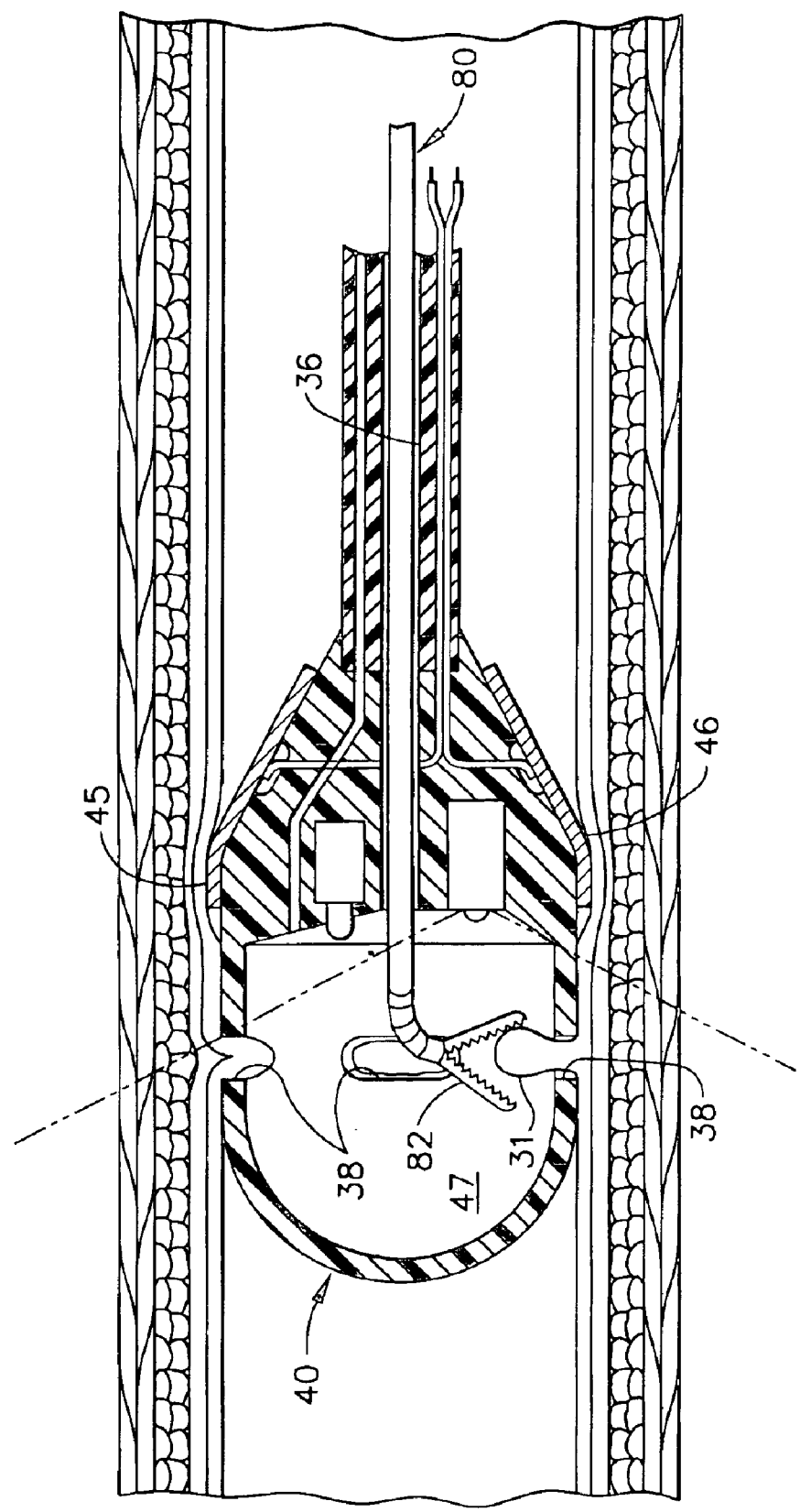
FIG. 9 is sectional view of capsule 40 inside of lumen 25 while a polyp 31 extends through a window 38 of capsule 40.

FIG. 3 is a sectional view of capsule 40 of FIG. 2, showing a distal portion 37 of working channel 36 connecting to a chamber 47 disposed within the capsule 40 and positioned near the leading end 43. A vacuum bore 71 can extend within the umbilicus 55, such as along side of working channel 36, to provide fluid communication between vacuum source 90 (see FIG. 2) and chamber 47 so that fluids and air may be evacuated from within the body lumen through windows 38, or to draw tissue structures such as a polyp into window 38 for access with instrument 80, as shown in FIG. 9. Alternatively, channel 36 could be employed to provide such fluid communication between vacuum source 90 and chamber 47, or vacuum bore 71 could be located externally of the umbilicus 55.

First electrode 45 and second electrode 46 are bonded relatively flush to trailing end 44 of capsule 40, and electrically connect to control unit 92 (FIG. 2) by wiring 93. The distal end of umbilicus 55 can be attached to trailing end 44 of capsule 40 by any suitable joining means. Umbilicus 55 is preferably made from a flexible plastic, multilumen tube. For example, umbilicus 55 may have three lumens: a 4 mm diameter lumen for working channel 36, a 2 mm diameter lumen for vacuum bore 71, and a 2 mm diameter lumen for wiring 93. Fluid system 97 (FIG. 2) may be fluidly connectable to working channel 36. Umbilicus 55 may also comprise separate thinwall, flexible plastic tubes and wires that are bundled together with straps, shrink wrap, or the like. To minimize the drag on capsule 40, umbilicus 55 should be lightweight, flexible, and relatively small in diameter.

FIG. 3 also shows a visualization device 49 and a lighting device 50 mounted inside of capsule 40. Visualization device 49 may be a CMOS (Complementary Metallic Oxide Semiconductor) or CCD (Charged Coupled Device) camera, either of which are commercially available in sizes adaptable to use in capsule 40. Visualization device 49 can be electrically connected to a power source, a signal-processing unit, and a display contained in control unit 92 (FIG. 2). In such an embodiment, leading end 43 of capsule 40 can be made of a transparent material such as clear polycarbonate. Lighting device 50 may be a single incandescent bulb or a plurality of LED's (light emitting diodes) electrically connected to a power source in control unit 92 (FIG. 2).

Still referring to FIG. 3, an angle "A" indicates the angular articulation necessary for the distal end of medical instrument 80 (see FIG. 9) extending through working channel 36 to access tissue structures through one of windows 38. Generally, Angle A can provide a measure of the orientation of a window 38 with respect to the longitudinal axis of working channel 36 as the working channel enters the capsule 40. Angle A may vary between about zero and about 90 degrees. In one embodiment, the angle can be at least about 30 degrees, more particularly at least about 45 degrees. In FIG. 3, one of the windows 38 is positioned relative to channel 36 to provide an angle A of about 90 degrees. In other embodiments, the capsule can be constructed with windows 38 or other openings to provide relatively "shallower" angles of access. For instance, a window 38 could be positioned at the most distal tip of the leading end of capsule 40 and be substantially aligned with the working channel 36, thereby providing an angle A of substantially zero degrees.

Figure 4:
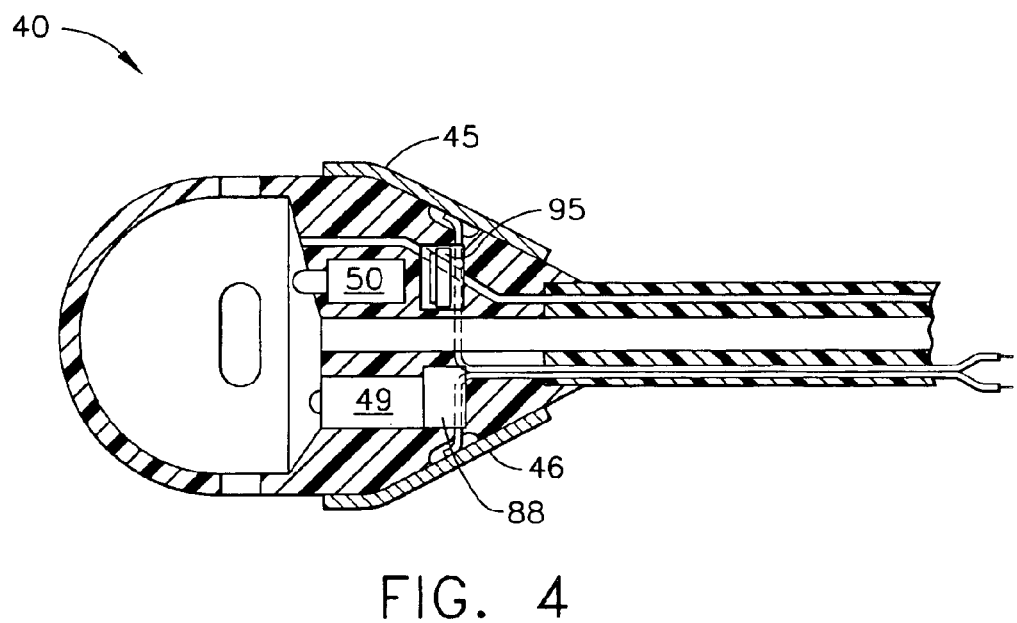
FIG. 4 is a sectional view of an alternate embodiment of capsule 40 shown in FIG. 2 and includes a battery 95 and a motion control unit 88.

FIG. 4 shows another embodiment of capsule 40 that includes a battery 95 for providing DC electrical power to lighting device 50 and/or visualization device 49, and an onboard electronics unit 88. Onboard electronics unit may be operationally associated with first electrode 45 and second electrode 46. Onboard electronics 88 may include one or more integrated circuits, and may replace or supplement one or more functions of control unit 92 shown in FIG. 2. For instance, but without limitation, onboard electronics 88 may include current or voltage control circuitry, temperature sensing electronics, or various feedback control circuitry devices.

Figure 5:
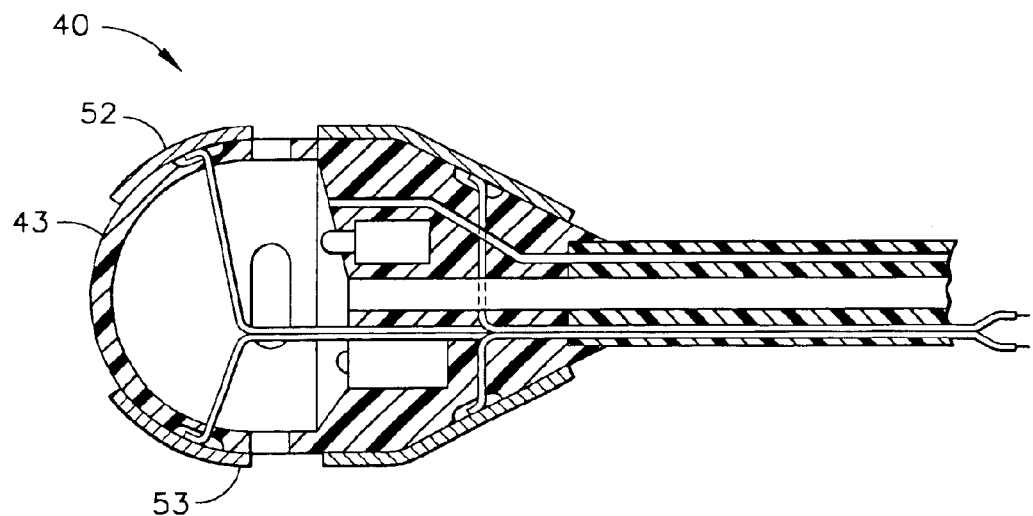
FIG. 5 is a sectional view of an alternate embodiment of capsule 40 shown in FIG. 2 and includes a third electrode 52 and a fourth electrode 53.

FIG. 5 is another embodiment of the present invention wherein capsule 40 includes a third electrode 52 having a first electrical polarity and a fourth electrode 53 having a second electrical polarity. Third electrode 52 and fourth electrode 53 electrically stimulate contractile tissue on a portion of the colon surrounding leading end 43 of capsule 40, for providing movement of capsule 40 in a reverse direction.

Figure 6:
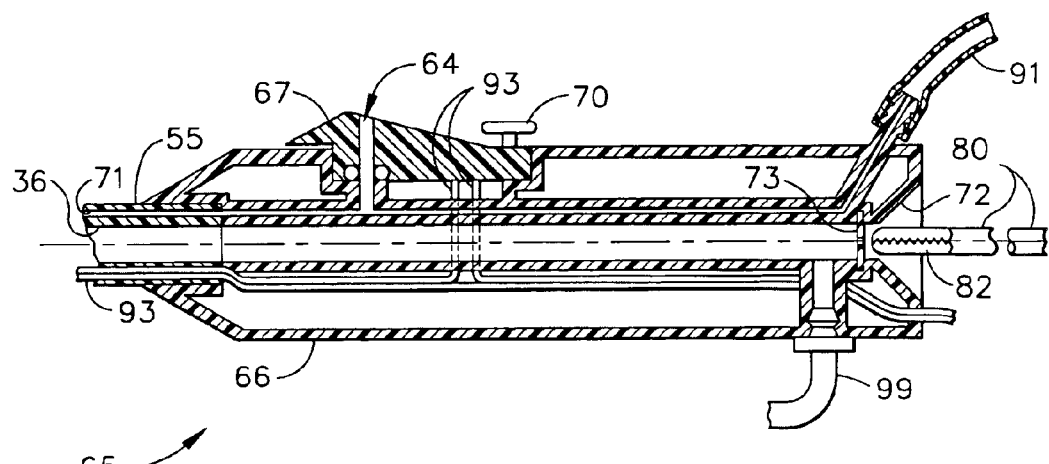
FIG. 6 is a sectional view of handpiece 65 shown in FIG. 2.

FIG. 6 is a sectional view of handpiece 65. The proximal end of umbilicus 55 can be attached to the distal end of handpiece 65, either by permanent means or by a releasable attachment mechanism (such as but not limited to threaded attachment, snap fit attachment, or other releasable attachment means) so that the handpiece can be used interchangeably with other devices, or if it is desirable for the umbilicus 55 to be releasably attached to the handpiece 65 so that handpiece can be packaged, cleaned, or provided separately from the umbilicus 55 and capsule 40. Likewise, umbilicus 55 can be attached to capsule 40 by permanent means or by releasable attachment means.

Working channel 36 can extend through at least a portion of the length of handpiece 65, and a seal 73 can be disposed in handpiece 65, such as in the proximal end of the handpiece 65. The seal 73 can be operatively associated with channel 36, such as for use in controlling inflow or outflow of air or other fluids (gaseous or liquid) through channel 36. For example, FIGS. 6 and 7 an end effector 82 of medical instrument in position for placement through seal 73. An inlet guide 72 of handpiece 65 facilitates placing end effector 82 through seal 73. Seal 73 closes the proximal end of working channel 36, but allows instrument 80 to sealingly pass into working channel 36. The operator may hold onto a grip 66 of handpiece 65 and use a finger or thumb to cover a bleed valve 64 on vacuum control 67 in order to communicate vacuum to capsule 40. When the operator uncovers bleed valve 64, vacuum bore 71 communicates with atmosphere, and vacuum is essentially disconnected from capsule 40. Fluid such as saline may be supplied from fluid system 97 (FIG. 2) into working channel 36 through fluid hose 99. Wiring 93 runs longitudinally from the proximal end of handpiece 65, to current control 70, and then to the distal end of handpiece 65 and into umbilicus 55. Hose 91 fluidly connects vacuum source 90 to vacuum bore 71.

Figure 7:
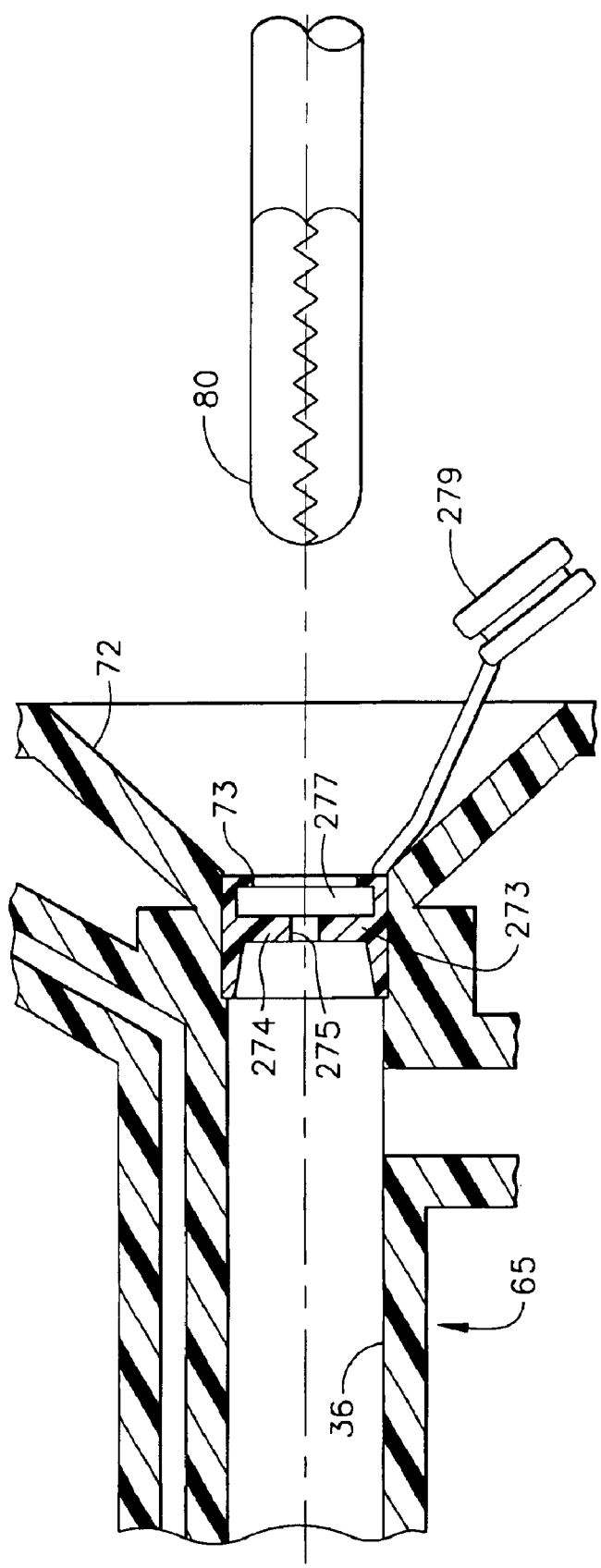
FIG. 7 is an enlarged view of a seal 73 shown in FIG. 6.

FIG. 7 is a sectional view of one possible embodiment of seal 73 in the proximal end of handpiece 65. Seal 73 may be made from silicone rubber or other suitable resilient material. Seal 73 can comprise a seal body 273 disposed in working channel 36. Seal body 273 includes a thin, flexible diaphragm 274 having a small aperture 275 that stretches upon insertion of instrument 80. Seal 73 also includes a seal cover 279, which may be retained in a seal cover cavity 277 when instrument 80 is withdrawn from handpiece 65, thus closing the proximal end of working channel 36.

Figure 8:
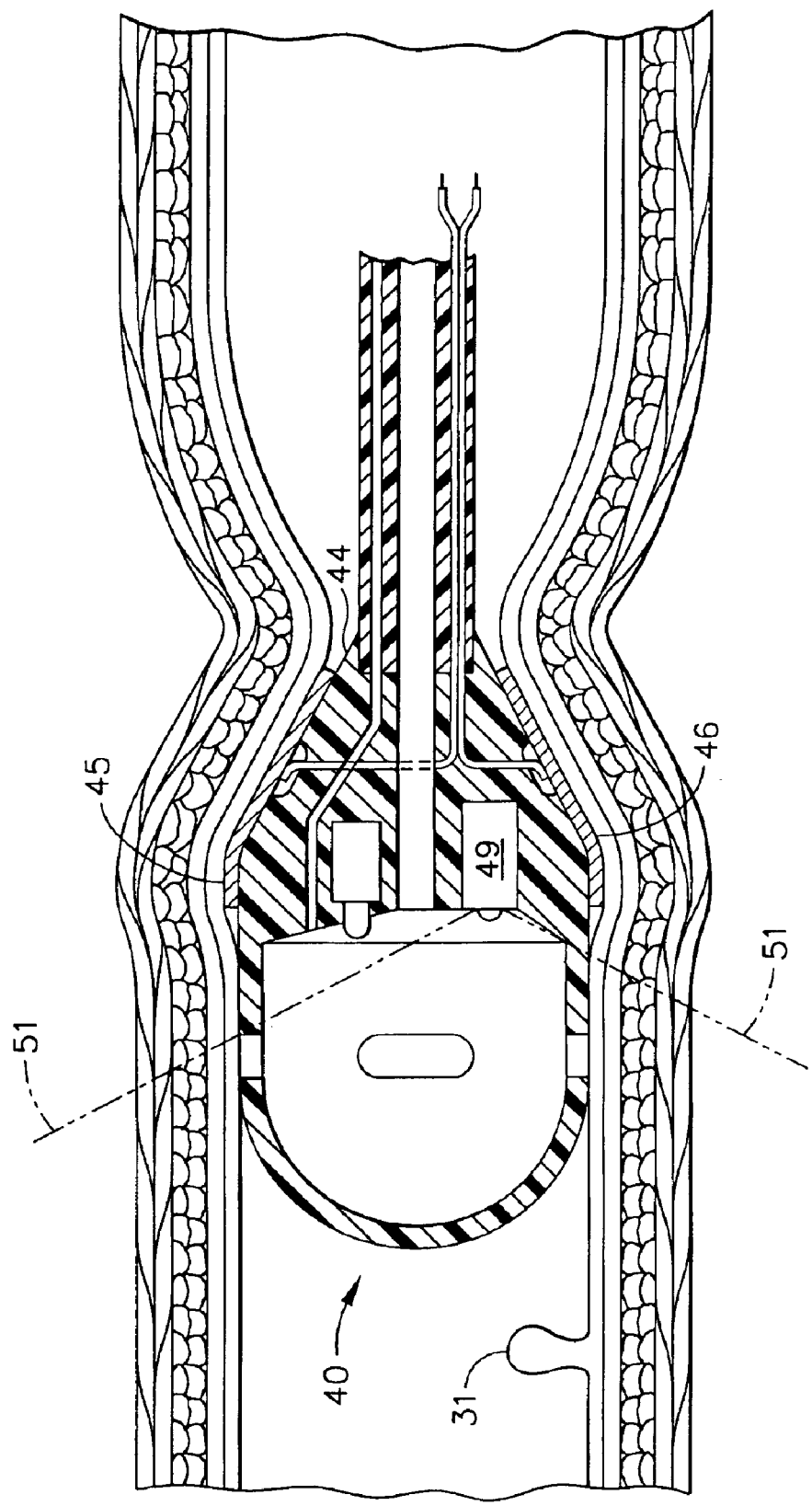
FIG. 8 is a sectional view of capsule 40 inside of a lumen 25 while wall 26 is electrically stimulated to propel (towards the left) capsule 40.

FIGS. 8 and 9 are sectional views of capsule 40 traversing the lumen of the colon. In FIG. 8, first electrode 45 and second electrode 46 are electrically energized and the colon is shown contracting around the trailing end 44 of capsule 40, thus pushing capsule 40 in a forward (left) direction. A field of view 51 of visualization device 49 is indicated with dashed lines. The operator may use motion control 68 on handpiece 65 (FIG. 2) to advance capsule 40 towards a polyp 31 within field of view 51. The operator may rotate capsule 40 along its longitudinal axis by rotating handpiece 65 so that tissue structures such as polyp 31 become aligned with one of windows 38. In FIG. 9 capsule 40 is shown positioned over polyp 31 and the colon is relaxed due to deactivation of first electrode 45 and second electrode 46. The operator may apply vacuum into chamber 47 to help draw polyp 31 into window 38. The operator may then articulate end effector 82 of instrument 80, grasp polyp 31, and remove polyp 31 through working channel 36, including the portion of the working channel in capsule 40.

Figure 10:
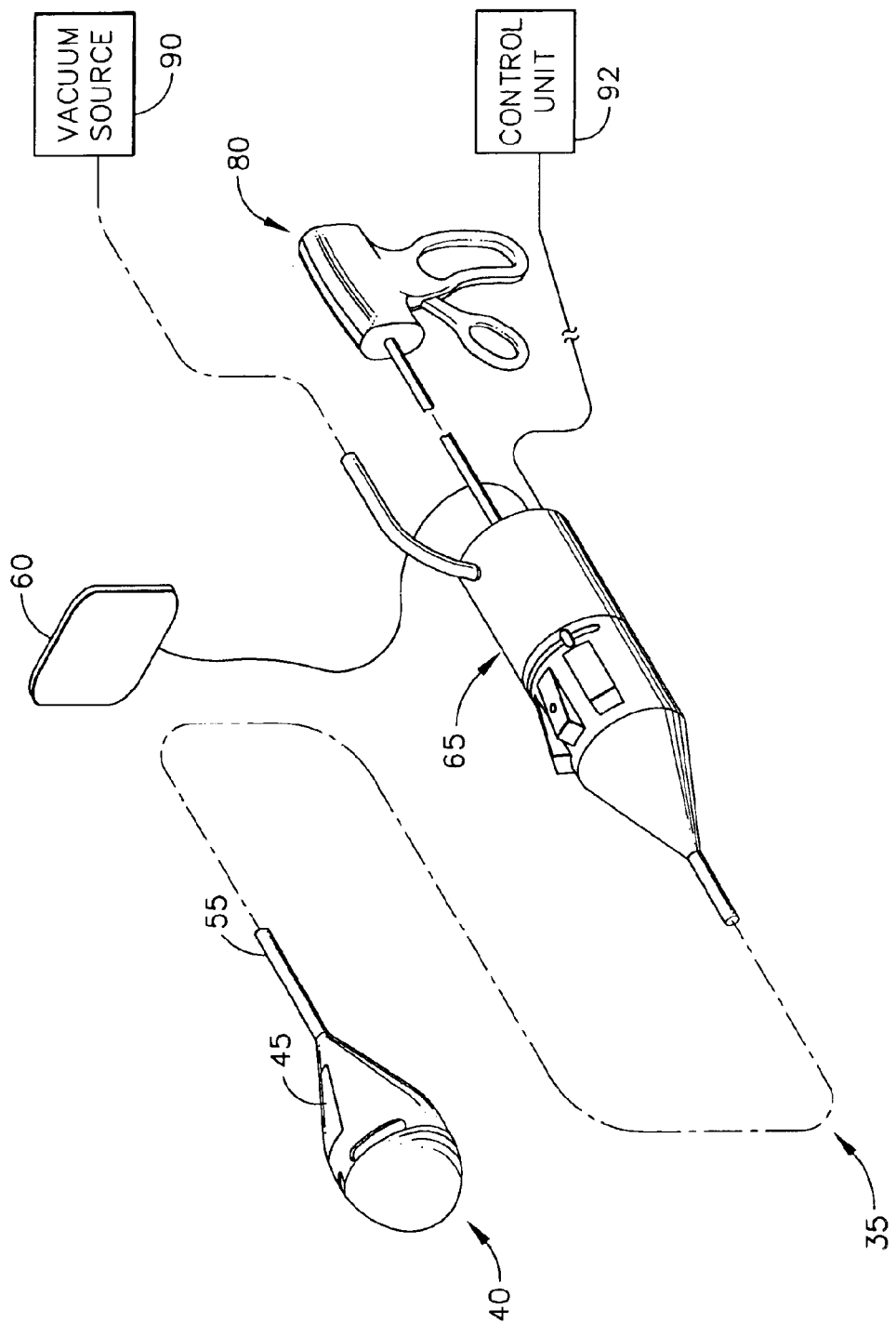
FIG. 10 shows an alternate embodiment of the present invention, including a patient electrode 60.

FIG. 10 shows another embodiment of medical device 35, which includes capsule 40, umbilicus 55, handpiece 65, control unit 92, and vacuum source 90. Capsule 40 includes a first electrode 45 having a first electrical polarity, and a patient electrode 60 having a second electrical polarity. Patient electrode 60 may be attached to an external surface of the patient such is done with the return electrode pad for conventional monopolar electrosurgery. The frequency, current, and waveform of the electrical energy transmitted to contractile tissue may be the same as described earlier for the embodiment shown in FIG. 2. Medical instrument 80 may also be introduced into handpiece 65 as described for FIG. 2.

Figure 11:
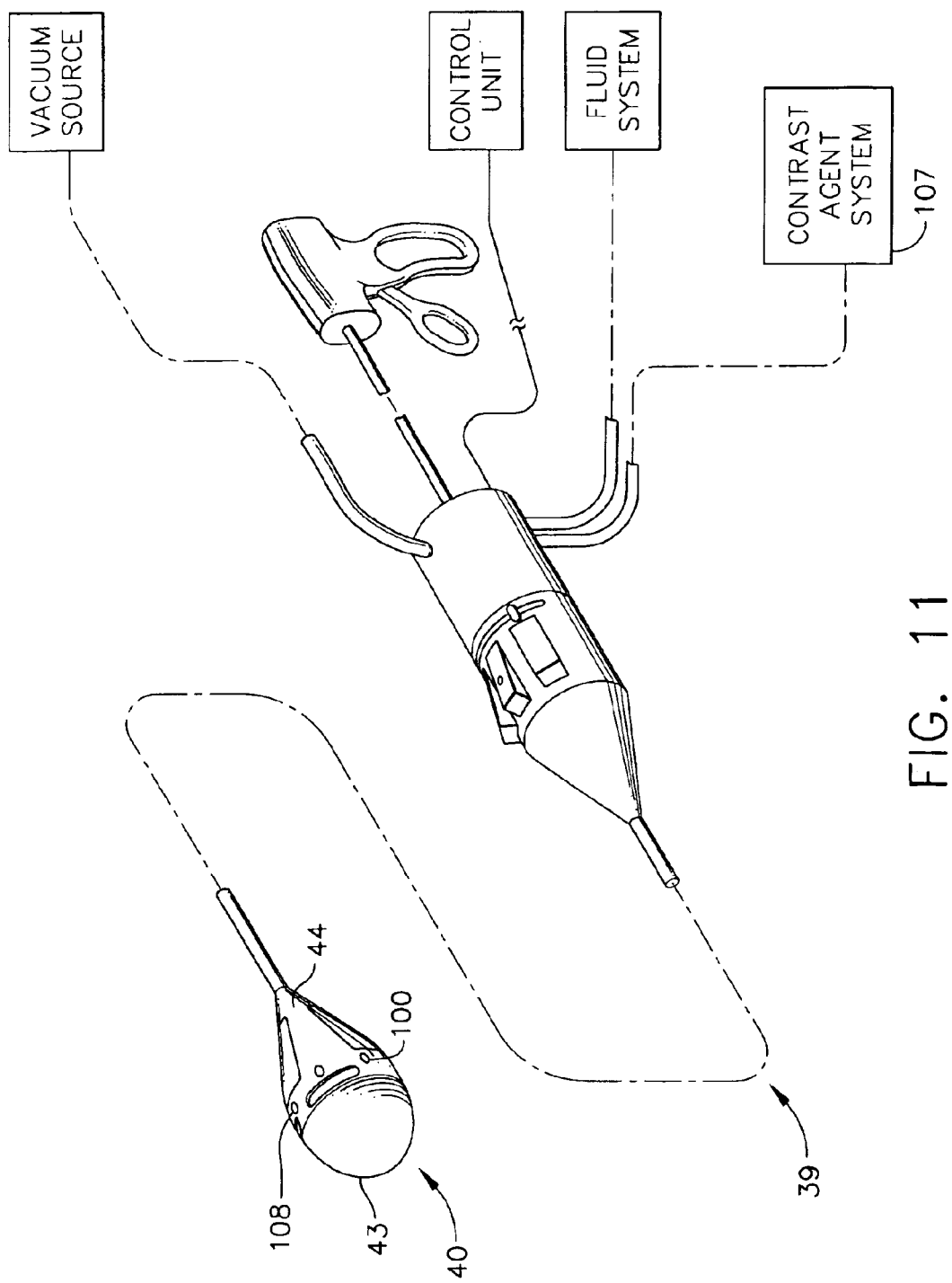
FIG. 11 shows a medical device 39 that is similar to medical device 35 of FIG. 2, and includes a diagnostic agent system 107 and a diagnostic agent applicator 108 in an alternate embodiment of capsule 40.

FIG. 11 shows a medical device 39 that is similar in many respects to the embodiments shown in FIGS. 2 and 10. Medical device 39 additionally includes a medical agent system 107 for introducing a medical agent, such as a diagnostic agent or therapeutic agent intraluminally through a medical agent applicator 108. For instance, medical agent applicator 108 can comprises one or more openings in the exterior of capsule 40, such as a plurality of weep holes 100 evenly spaced around the circumference of capsule 40 approximately midway between trailing end 44 and leading end 43. In FIG. 11 medical agent system 107 is designated as a contrast agent system for illustration purposes, but it will be understood that medical agent system can be used to dispense one or more diagnostic and/or therapeutic agents, and is not limited to application of contrast agents.

FIGS. 12, 13, and 14 are sectional views of capsule 40 and the distal portion of umbilicus 55 for medical device 39 of FIG. 11. Capsule 40 again includes first electrode 45, second electrode 46, lighting device 50, visualization device 49, wiring 93, vacuum bore 71, windows 38, chamber 47, leading end 43, and trailing end 44. A channel 101 extends through umbilicus 55 and into medical agent applicator 108 of capsule 40, that includes a circular manifold 102 fluidly connected to plurality of weep holes 100. Channel 101 fluidly connects to tube 104 inside of handpiece 65. Tube 104 fluidly connects to medical agent system 107, which includes a reservoir filled with diagnostic agent and a valve (not shown) for supplying diagnostic agent to medical device 39. The reservoir of diagnostic agent system 107 may comprise an electric pump, a syringe, or an elevated bag with an on/off valve for supplying diagnostic agent to capsule 40. Medical device 39 optionally includes working channel 36 as described for the previous embodiments.

Diagnostic agents/therapeutic agents that may be used with medical agent system 107 include standard tissue dyes such as, for example, methylene blue stain (catalog number MB119, Molecular Research Center, Inc., Cincinnati, Ohio) and indigo carmine (product code C111, ProSciTech, Kelso, Qld, 4851, Australia.) The diagnostic agent can be a liquid or a gel containing a fluorescent or radiological material, or any other material that can aid in identifying diseased tissue. Additionally, any one of a number of other materials can be applied intraluminally using fluid system 97 or system 107, including muscular contraction agents, antibiotics, analgesics, and oncology pharmaceuticals.

The operator may apply diagnostic agent to the mucosal layer of a portion or the entire length of a body lumen such as the colon by using the following steps. The operator introduces capsule 40 into the body lumen. When introducing capsule 40 into the colon, the operator may use conventional instruments, lubrication and techniques to pass capsule 40 and a portion of umbilicus 55 through the anus and rectum of the sedated patient, who is lying on one side. The operator may also introduce lubricating agents through the fluid system 97 above to assist in introducing the capsule into the body lumen. The operator next activates control unit 92 to move capsule 40 and trailing umbilicus 55 in a forward direction through the body lumen. The operator then opens the fluid connection between medical agent system 107 and capsule 40 to introduce diagnostic agent into the body lumen. The operator monitors the movement of capsule 40 in the forward direction as the diagnostic agent is dispensed. The operator may note the length of umbilicus introduced into the body lumen to determine the distance capsule 40 has moved. The operator may also observe the amount of diagnostic agent remaining in the reservoir of system 107 to know that diagnostic agent is being properly dispensed. When the operator has determined that capsule 40 has moved a sufficient distance through the body lumen, the operator closes the fluid connection between capsule 40 and system 107 and deactivates control unit 92. The operator then pulls umbilicus 55 carefully to move capsule 40 in the reverse direction, and removes capsule 40 and umbilicus 55 from the body lumen. The foregoing method may also have the additional steps of visualizing inside of the body lumen as capsule 40 moves in either the forward or reverse directions. The operator may also dispense diagnostic agent while pulling capsule 40 in the reverse direction instead of dispensing diagnostic agent while capsule 40 moves in the forward direction. The operator may optionally use the fluid system provided to flush the lumen with clean water or a saline solution to remove excess diagnostic agent and further highlight the tissue of interest. The body lumen next is ready for endoscopic examination, using the visualization means of the present invention, or using a conventional, flexible endoscope.

The medical apparatus of the present invention can be adapted to releasably receive medical instruments other than the surgical instrument 80 shown. Medical instruments useful in combination with the present invention include, but are not limited to: those that provide images (light, sound) of a treatment sight); those that collect samples of tissue or fluid, such as biopsy forceps and other biopsy devices; those that dispense medicinal or non-medicinal compositions or objects at a treatment site (e.g. pharmaceuticals, stains, tissue markers, or cleaning compositions); and those that provide surgical cutting (including without limitation ultrasonic, radio-frequency and laser cutting), cauterizing, ligation, suturing, surgical snaring, tissue joining, and/or stapling functions. It will be understood that the size and shape of passageway 36 can be adapted to accommodate different types of medical instruments.

In the embodiments described above, the lumen tissue stimulating device employs an electrical stimulus to facilitate travel of the capsule 40 through the lumen. In other embodiments, other stimuli may be used, including without limitation, sonic energy (such as ultrasonic energy), light energy, or chemical stimuli (such as by controlled deposition of a liquid from the capsule 40 to the lumen wall to cause contraction of the lumen wall).

It will be recognized that equivalent structures may be substituted for the structures illustrated and described herein and that the described embodiment of the invention is not the only structure which may be employed to implement the claimed invention. In addition, it should be understood that every structure described above has a function and such structure can be referred to as a means for performing that function.

While we have disclosed numerous embodiments of the present invention, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A medical device comprising:
   a propulsion member;
   a flexible elongate member;
   wherein the propulsion member is disposed at a distal end of the relatively flexible elongate member, and wherein the propulsion member is adapted to provide a pronulsion force distal of the flexible elongate member for advancing the propulsion member in a body lumen of patient; and
   a working channel extending through the length of the flexible elongate member and through at least a portion of the propulsion member, the working channel sized for receiving a medical instrument for providing access to at least a portion of the body lumen through the propulsion member from a point outside the patient's body.

2. The medical device of claim 1 comprising a vacuum source operatively associated with the propulsion member for communicating vacuum to the body lumen.

3. The medical device of claim 1 wherein the propulsion member is self propelled by stimulation of tissue within the lumen.

4. The medical device of claim 1 comprising at least one electrode for facilitating movement of the propulsion member through the body lumen.

5. The medical device of claim 1 wherein the flexible elongate member comprises an umbilicus.

6. The medical device of claim 1 wherein the working channel communicates with at least one opening in an exterior surface of the propulsion member.

7. The medical device of claim 6 wherein the working channel communicates with multiple openings in the exterior surface of the propulsion member.

8. The medical device of claim 6 wherein at least one opening in the exterior surface of the propulsion member has an axis forming an angle of at least about 30 degrees with respect to the longitudinal axis of a portion of the working channel.

9. The medical device of claim 6 wherein at least one opening in the exterior surface of the propulsion member is positioned to provide access through a side portion of the propulsion member.

10. A medical device comprising:
    a capsule for introduction into a patient's body lumen;
    at least one electrode for electrically stimulating tissue to provide movement of the capsule;
    an umbilicus attached to said capsule, said umbilicus of sufficient length to extend outside of said body lumen while said capsule is inside of said body lumen; and
    at least one generally continuous working channel extending through the umbilicus and a least a portion of the capsule, wherein the working channel is adapted to provide access by a medical instrument to the lumen through the capsule from a point outside the patient's body.

11. The medical device of claim 10 comprising a visualization device and a lighting device for visualizing inside of the body lumen.

12. The medical device of claim 10 comprising a vacuum source in operative association with the capsule.

13. The medical device of claim 10 comprising a fluid system for introducing a fluid to the inside of the body lumen.

14. The medical device of claim 10 comprising a fluid seal operatively associated with said working channel.

15. The medical device of claim 10 comprising at least one external electrode for electrical contact with an external surface of the patient.

16. The medical device of claim 10 comprising at least one electrode mounted on said capsule.

17. The medical device of claim 10 comprising a handpiece operably attached to the proximal end of said umbilicus, wherein said working channel extends through at least a portion of the handpiece.

18. The medical device of claim 17 wherein said handpiece includes at least one control selected from the group consisting of vacuum controls, fluid controls, motion controls, electrical stimulation current controls, and electrical stimulation frequency control.

19. A method of accessing tissue in a body lumen with a medical instrument, the method comprising the steps of:
    providing a flexible elongate member;
    providing a propulsion member at a distal end of the flexible elongate member;
    providing a working channel extending through the flexible elongate member;

positioning the propulsion member in the body lumen;

providing a force distal of the flexible elongate member for advancing the propulsion member in the body lumen; and directing a medical instrument from a point outside the body through the working channel in the flexible elongate member to access tissue in the lumen through an opening in the propulsion member.

20. The method of claim 19 wherein the step of providing a force distal of the flexible elongate member comprises stimulating tissue.

21. The method of claim 19 further comprising drawing tissue into a portion of the propulsion member.

22. The method of claim 19 wherein the medical instrument is selected from the group consisting of surgical cutting instruments, surgical ligation instruments, surgical biopsy instruments, surgical suturing instruments, and combinations thereof.

23. The method of claim 19 comprising the step of surgically removing a portion of the patient's body.

24. The method of claim 19 comprising surgically removing a portion of the patient's body through the propulsion member.

* * * * *